(12) United States Patent
Moore et al.

(10) Patent No.: US 9,481,609 B2
(45) Date of Patent: Nov. 1, 2016

(54) HETEROMORPHIC LYSINE FEED GRANULES

(71) Applicant: ARCHER DANIELS MIDLAND COMPANY, Decatur, IL (US)

(72) Inventors: Kevin Moore, Mt. Zion, IL (US); Sundeep N. Vani, Champaign, IL (US); Kenneth E. Tague, Mt. Zion, IL (US)

(73) Assignee: Archer Daniels Midland Company, Decatur, IL (US)

( * ) Notice: Subject to any disclaimer, the term of this patent is extended or adjusted under 35 U.S.C. 154(b) by 181 days.

(21) Appl. No.: 13/950,355

(22) Filed: Jul. 25, 2013

(65) Prior Publication Data

US 2013/0305793 A1 Nov. 21, 2013

Related U.S. Application Data

(63) Continuation of application No. 12/237,820, filed on Sep. 25, 2008, now abandoned.

(60) Provisional application No. 60/995,561, filed on Sep. 27, 2007.

(51) Int. Cl.
| | | |
|---|---|---|
| *A23B 4/12* | (2006.01) |
| *A23J 3/34* | (2006.01) |
| *A23L 1/216* | (2006.01) |
| *A23K 1/18* | (2006.01) |
| *A23J 1/00* | (2006.01) |
| *A23L 1/30* | (2006.01) |
| *C05B 17/00* | (2006.01) |
| *C05F 11/10* | (2006.01) |
| *C05G 3/00* | (2006.01) |
| *C12P 13/08* | (2006.01) |
| *C05C 11/00* | (2006.01) |

(52) U.S. Cl.
CPC ............. *C05B 17/00* (2013.01); *A23K 20/142* (2016.05); *A23K 40/10* (2016.05); *A23K 40/30* (2016.05); *A23K 50/10* (2016.05); *C05C 11/00* (2013.01); *C05F 11/10* (2013.01); *C05G 3/0041* (2013.01); *C05G 3/0047* (2013.01); *C12P 13/08* (2013.01)

(58) Field of Classification Search
CPC .... A23K 40/10; A23K 40/30; A23K 20/142; A23K 50/10
USPC ................. 426/69, 648, 97, 2, 656
See application file for complete search history.

(56) References Cited

U.S. PATENT DOCUMENTS

| | | | | |
|---|---|---|---|---|
| 5,622,710 A | * | 4/1997 | Binder et al. ................. 424/438 |
| 2007/0131010 A1 | * | 6/2007 | Binder et al. ..................... 71/23 |
| 2007/0160740 A1 | * | 7/2007 | Lee et al. ...................... 426/635 |

FOREIGN PATENT DOCUMENTS

EP 491638 A2 * 6/1992

\* cited by examiner

*Primary Examiner* — Erik Kashnikow
*Assistant Examiner* — Assaf Zilbering
(74) *Attorney, Agent, or Firm* — Corey Crafton

(57) ABSTRACT

A heteromorphic granule comprising lysine free base and a lysine salt is disclosed. A fertilizer composition is set forth having cores containing an acid salt of a basic amino acid and effective amounts of first and second layer coatings coated sequentially to the surface of each core. A method for using the heteromorphic granule as a fertilizer and/or an animal feed is provided.

10 Claims, 11 Drawing Sheets

A     B     C     D     E

Examples of particle morphologies.
- A- core-shell particle or "onion" morphology with transition gradient interlayer.
- B- "raspberry" morphology
- C- "salt and pepper morphology"
- D- Interpenetrating network
- E- Lobed particles

HETEROMORPHIC LYSINE FEED GRANULES

CROSS-REFERENCE TO RELATED APPLICATION

This application is a continuation of U.S. application Ser. No. 12/237,820 now abandoned, which claims the benefit of U.S. patent Application Ser. No. 60/995,561 filed Sep. 27, 2007. The Entire contents of U.S. Patent Application Ser. No. 60/995,561 is incorporated by reference into this application.

FIELD OF THE INVENTION

This disclosure is directed towards free flowing animal feed supplements containing mixtures of various amino acids or those of freebase amino acids intermixed with salts of amino acids.

BACKGROUND

The following background material includes information that may be useful in understanding the present teaching. It is not an admission that any of the information provided herein is prior art, or material, to the presently described or claimed disclosures, or that any publication or document that is specifically or implicitly referenced is prior art.

L-lysine is an essential amino acid that is supplied as a feed supplement for both monogastric and ruminant animals. lysine feed supplements are commercially supplied in essentially three forms—as dried granules of lysine-HCl salt (often called merely lysine HCL), as a dried broth from a fermenter from which the lysine was made by bacterial fermentation (often referred to as lysine sulfate because the predominant form of the lysine from a dried broth is as a sulfate salt) and finally as free lysine that is supplied as liquid solution to be sprayed onto animal feed as a supplement (often called lysine freebase). There are minor variations in some compositions of these three forms of lysine feed. For example, lysine HCl granules may include minor amounts of anti-caking agents to improve flow properties, dried lysine sulfate may or may not include the bacterial cell mass from the fermentation broth, and lysine freebase may be supplied in different liquid concentrations.

Each of the three forms of commercially available lysine feed supplements have advantages and disadvantages. Some advantages of lysine HCl are that the dried granules are relatively speaking, pure, inexpensive to ship, easy to control in terms of production specifications, and have low hygroscopic character. The major disadvantages are that it is costly to make because it requires purification and crystallization of lysine from a fermentation broth, and only 80% of the weight of the product is lysine—the remainder being the HCl. The major advantage of lysine sulfate is that it is simplest to make, however, its disadvantages are that the product has variable composition because it is simply a dried fermentation broth, and for the same reason is relatively impure, with typically no more than 50% of the dry weight of the product being lysine. The major advantages of lysine freebase are that the lysine product in solution high purity, and the ease of shipping and handling a liquid. The major disadvantages of lysine freebase is that because it is provided as a solution, shipping costs on a lysine content basis are higher than for the other dry products, and that dedicated mixing equipment is needed to dispense the product onto animal feed.

lysine may also be used in the agricultural industry as a fertilizer. The nitrogen content of lysine is sufficient for practical use as fertilizer, which has the advantages of being organic, biodegradable and a source of nutrition for soil microbes. lysine alone, however, lacks other mineral ingredients such as potassium and phosphate that are often added to a fertilizer. The same advantages and disadvantages of the three forms of lysine mentioned above apply equally when the product is used as a fertilizer.

Although it would seem desirable to sell lysine freebase as a dried product to lower shipping and production costs, from a commercial standpoint such a product is not desirable because lysine freebase is much more hygroscopic than lysine HCl or lysine sulfate, causing the product to cake, swell and loose the free flowing properties that make a dried product easy to manage and dispense. There is therefore, a need in the art to provide a dried lysine feed product that has at least some of the advantages of lysine freebase but without the disadvantages that make such a product undesirable.

The present disclosure addresses this need and others that will be apparent from the disclosure that follows.

SUMMARY

Described herein are various embodiments of heteromorphic lysine granules and mixtures. These embodiments are a combination of dried lysine freebase blended with—or agglomerated into a layered structure with—various amounts of lysine HCl, salt particles, other amino acids or other crude sources of lysine. These heteromorphic granules and mixtures offer many of the advantages of lysine HCl in terms of ease of use and low hygroscopic character, while providing at least a portion of the advantages of lysine freebase in terms of purity and ease of production. The teachings of this disclosure are concerned with new lysine products that incorporate dried lysine freebase. Currently there are two forms of soft lysine widely accepted in the marketplace: (1) lysine HCl, which is a crystalline and dried salt of lysine, and (2) liquid lysine, which is a concentrated solution of substantially pure lysine freebase in water. It is a generally accepted fact that lysine freebase is simpler to manufacture (on a pure lysine basis) because the manufacture of salts of lysine such as lysine HCl requires several additional processing steps. However, these advantages are somewhat offset by additional transportation costs incurred in delivering liquid lysine. Additionally the handing of lysine freebase requires an investment in additional infrastructure for the customer. Hence, in general lysine freebase is viable for only large volume customers.

The ability of a dried form of lysine freebase that is free flowing and does not exhibit significant caking properties is important aspect of the process for increasing the application of lysine freebase for small volume customers.

In one aspect a composition comprising a granule of a dried lysine salt admixed with dried free lysine freebase wherein the lysine salt comprises between 10 percent and 80 percent of the granule is described. In certain embodiments the composition may comprise a granule that has a core of a dried lysine freebase surrounded by a coating of a dried lysine salt.

In another aspect a composition comprising a granule having an inner core containing a first fraction of a dried lysine salt, a medial layer coating the core comprised of a dried lysine freebase, and an outer layer coating the medial layer comprised of a second fraction of dried lysine salt is described. In certain embodiments, the composition may comprise a granule of a dried threonine admixed with dried free lysine freebase wherein the lysine freebase comprises between 10 percent and 80 percent of the granule. In certain other embodiments the composition may comprise a granule of a dried threonine admixed with dried lysine salt wherein the lysine salt comprises between 10 percent and 80 percent of the granule. In certain other embodiments a composition comprising a granule of a dried threonine admixed with dried lysine salt and dried free lysine freebase wherein the lysine components, comprise between 10 percent and 80 percent of the granule is described.

In another aspect a method is described where a fermentation is done with a microorganism to produce a fermentation broth containing a cell mass and a soluble lysine fraction; followed by a method to separate the cell mass from the solublized lysine fraction; followed by purifying the solublized lysine fraction and neutralizing a portion of the solublized lysine fraction with a mineral acid to produce a lysine salt. Certain embodiments may additionally include a method for spray agglomerating the solublized lysine fraction and lysine salt to produce heteromorphic lysine granules.

In another aspect a composition is described which comprises a granule that has a core of a dried lysine salt surrounded by a coating of a dried lysine freebase. In certain embodiments the composition may also comprise a granule that has a core of a dried lysine freebase surrounded by a coating of a dried threonine freebase. In certain other embodiments the composition may comprise a granule that has a core of a dried threonine freebase surrounded by a coating of a dried lysine salt.

In other aspects are described compositions comprising dried lysine freebase that absorbs less than 10% water when exposed to a temperature of 10 degrees Celsius to 50 degrees Celsius and a humidity of between 30% and 91% relative humidity for a period of 24 to 168 hours.

In certain embodiments lysine and salts of lysine may be produced by a fermentation of *Corynebacterium glutamicum* In certain other embodiments the threonine may be produced by *Escherichia Coli* fermentation.

In certain yet other aspects a method is described for the use of a composition comprising granules of dried lysine freebase coated with a lysine salt for at least one application selected from the group consisting of a fertilizer and an animal feed. Certain embodiments may include a feed additive for ruminants, that consists essentially of cores containing an acid salt of a basic amino acid, and effective amounts of a first coating layer and a second coating layer coated sequentially on the surface of each core, wherein said first coating layer contains at least one first coating agent selected from the group comprising salts of a basic amino acid, freebase of an amino acid, alkali metal salt, nitrogen source, phosphate source, potassium source, and the second coating layer contains as a second coating agent selected from the group comprising salts of a basic amino acid, freebase of an amino acid, alkali metal salt, nitrogen source, phosphate source, potassium source.

In certain embodiments the first coating agent may be at least one amino acid selected from the group comprising methionine, leucine, isoleucine and tryptophan. In certain embodiments the second coating agent is at least one amino acid selected from the group comprising methionine, leucine, isoleucine, valine, cysteine, tryptophan, threonine and phenylalanine. Other embodiments include a free-flowing powder of a lysine freebase, having irregular nonspherical morphology coated with a layer of salt of lysine and a particle size distribution ranging from 10 μm to 800 μm.

Certain other embodiments include a free-flowing powder of a salt of lysine, having irregular nonspherical morphology coated with a layer of lysine freebase and a particle size distribution ranging from 10 μm to 800 μm. Certain yet other embodiments include a free-flowing power of a lysine freebase, having multiphase morphology of roughly spherical shape that comprises alternating layers of lysine freebase and lysine hydrochloride or threonine arranged concentrically. In certain embodiments a free-flowing power of a salt of lysine, having multiphase morphology of roughly spherical shape that comprises alternating layers of lysine freebase and a salt of lysine or threonine arranged concentrically are described. Certain embodiments may include heteromorphic granules of lysine or threonine that have a morphology selected from core-shell, gradient, ice-cream cone, raspberry, salt and pepper or onion. In certain embodiments the granules may have more than one type of morphologies. Certain yet other embodiments may include heteromorphic granules of lysine or threonine that are additionally co-coated with mineral salts. In certain embodiments, the salts may provide nitrogen, phosphorous and potassium nutrients to the granules. Additional embodiments describe heteromorphic granules that have an N-P-K ratio of 1:1:1. In some embodiments the N-P-K ratio may be 2-1-1, 3-1-1, 3-2-1 or 2-3-1. Also described herein are processes for producing the heteromorphic granules described herein.

Additional embodiments include producing the heteromorphic granules at a first location; and transporting the composition to a second location. In certain other embodiments the first location and the second location may be countries.

Additional embodiments describe lysine granules that are produced by a micro-organism that is not genetically modified. Yet additional embodiments include a facility operatively configured to perform the process or make the compositions described herein.

DETAILED DESCRIPTION

Definitions

Prior to describing the present invention in detail, certain terms that have plain meanings generally understood by those of ordinary skill in the art are nevertheless defined herein to better distinguish nuances in meaning intended by the inventors. It is understood that the definitions provided herein are intended to encompass the ordinary meaning understood in the art without limitation, unless such a meaning would be incompatible with the definitions provided herein, in which case the provided definitions control.

"About" when used with reference to a numerical expression, means the greater of: (1) the degree of error of a typical instrument or process used to measure the items referenced by the expression; (2) plus or minus 10% of the stated value; or (3) with respect to a range, near enough to the minima or maxima of the range so as not to have any noticeable difference in form or function in comparison to an element exactly at the stated minima or maxima.

"Dry" or "Dried" means a material has a moisture content of less than 15% wt/wt, or has been treated to reduce the moisture content of the material to less than 50% the moisture content of the same material not so treated.

The term "lysine" means the amino acid lysine ($C_6H_{14}N_2O_2$) and salts or derivatives thereof, and includes all isomers of lysine (i.e., L-lysine, D-lysine, and any mixture of L- and D-lysine).

For convenience of expression, the term "dryer" will hereafter be used to describe any suitable drying means such as a spray dryer, drum dryer, tunnel dryer, rotary dryer, tray dryer, and spray granulator.

The terms "spray granulation". "spray granulation step", and "agglomeration" will hereafter be regarded as equivalent terms.

The term "separation" when applied to a fermentation broth will hereafter be used to describe the separating of a lysine fermentation broth into two fractions: a cell rich lysine broth and a substantially cell free lysine broth. Any suitable separating means or combination of separating means may be used. Separation may be achieved by means of filtration (e.g. ultra- and microfiltration), and mechanical methods such as centrifugation, hydroclones, rotary vacuum filters, settling tanks, depth filters and decanting.

The terms "evaporation" and "evaporated" will hereafter be used to describe the removal of water by evaporation, which is carried out in the approximate temperature range of between 140 degree F. and 214 degree F., with a pressure between 2.9 psia and 11 psia (vacuum).

The terms "lysine hydrochloride" and "lysine HCL" will hereafter be regarded as equivalent terms.

The terms "lysine sulfate" and "lysine $H_2SO_4$" will hereafter be regarded as equivalent terms.

The term "lysine freebase" means the amino acid lysine in the absence of a neutralizing salt.

The term "material containing lysine" will hereafter be used to describe any material of manufacture that contains any form of lysine alone or in combination with other materials and is commercially used at least in part for delivery of lysine. Suitable forms of lysine in a material containing lysine include, but are not limited to, a lysine fermentation broth with or without cell mass, a dried lysine fermentation broth, lysine hydrochloride, lysine sulfate, and/or lysine freebase.

The term "final lysine feed supplement" will hereafter be used to describe a commercially available material containing lysine f having a lysine of a purity within a range between about 15% and 80% lysine, measured as a percent of lysine by weight of material, and which is used to supplement feed for a non-human animal.

DESCRIPTION OF EXEMPLARY EMBODIMENTS

One aspect of this teaching provides a free flowing dried amino acid product containing lysine that exhibits reduced caking properties in comparison to dried lysine freebase alone. Various embodiments focus on a heteromorphic lysine granule product with greater pourability over lysine freebase alone and higher lysine content than lysine salt products alone. In certain embodiments the granules are a combination of lysine freebase, and a salt of lysine, and/or with threonine or a salt of threonine. Other embodiments may include pure free dry freebase lysine or blends of lysine freebase and a salt of lysine such as lysine hydrochloride with a concentration of lysine freebase ranging from 10 percent by weight to 100 percent by weight.

Pure dry lysine freebase may be used to make the granules. "Pure" in this context means at least 90% of the dry weight of the material is lysine freebase. As the proportion of lysine freebase is increased the cost savings associated with manufacturing the product are expected to be higher. Blending of a salt of lysine is usually required to modify the handling characteristics of the blend so that the final product is easy to handle and package. One especially desired aspect is improvement in the flowability, pourability and anticaking properties of the blends during packaging, storing and handling.

In one aspect lysine granules of "onion morphology" or core-shell morphology may be produced. Onion morphology may be a multiphase morphology of roughly spherical shape that comprises alternating layers of different forms of lysine or threonine arranged concentrically, typically with all layers being of similar thickness. In an embodiment the different forms of lysine may comprise lysine freebase, lysine hydrochloride, lysine sulfate or lysine cell broth. In another embodiment threonine or different forms of threonine may be used. In yet another embodiment, various mineral salts that provide a nutritive value in animal feed may also be used. Such salts may include a solid potassium salt, such as potassium chloride, mixed with an ammonium nitrate-containing liquid or solid salt phase that also contains ammonium phosphate, or to which ammonium phosphate may also be added.

Figure 1:
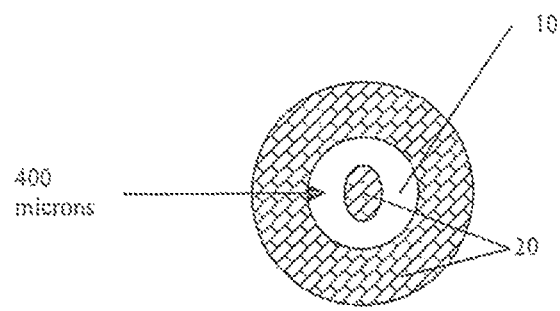
FIG. 1 is a schematic of granulated lysine feed product comprising lysine salt 20 core surrounded by lysine freebase 10 shell covered by another shell of lysine salt 20.
Figure 2:
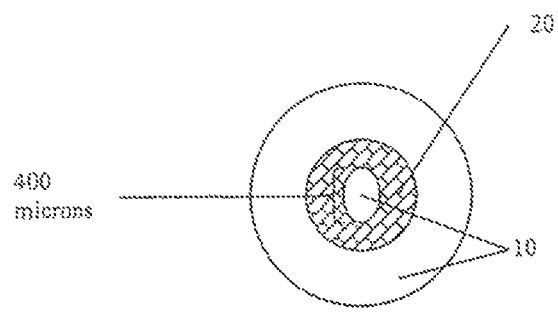
FIG. 2 is a schematic of granulated lysine feed product comprising lysine freebase 10 core surrounded by lysine hydrochloride 20 shell covered by another shell of lysine freebase 10.

Various morphologies of lysine granules may be of the type shown in non-limiting embodiments depicted in FIGS. 1-12. For instance, as depicted in FIG. 1, a roughly spherical shape morphology may comprise a core of lysine hydrochloride 20 surrounded by a shell of lysine freebase 10 and a second shell of lysine hydrochloride 20. An alternative embodiment, as depicted in FIG. 2, may be a roughly spherical shape comprising a core of lysine freebase 10 surrounded by a shell of lysine hydrochloride 20 and a second shell of lysine freebase 10. The inner cores may in certain embodiments, be about 400 microns in diameter. In certain other embodiments the granules may be between 10 microns to 800 microns.

Figure 3:
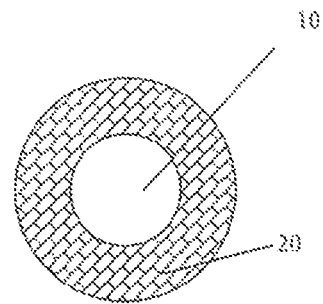
FIG. 3 is a schematic of granulated lysine feed product comprising lysine salt 20 core surrounded by lysine freebase 10 shell.
Figure 4:
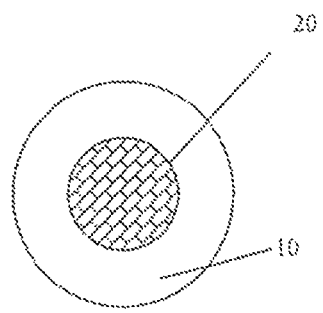
FIG. 4 is a schematic of granulated lysine feed product comprising lysine freebase 10 core surrounded by lysine salt 20 shell.

In another non-limiting embodiment, a core of lysine freebase 10 may be surrounded by a shell of lysine hydrochloride 20 as depicted in FIG. 3, or a core of lysine hydrochloride 20 may be surrounded by a shell of lysine freebase 10 as depicted in FIG. 4.

Figure 5:
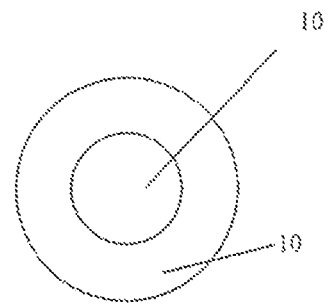
FIG. 5 is a schematic of granulated lysine feed product comprising lysine freebase 10 core surrounded by lysine freebase 10 shell.

One embodiment of the onion morphology may comprise a core of lysine freebase 10 coated with a single outer layer (shell) of lysine hydrochloride 20 as depicted in FIG. 5, resulting in improved flow properties.

Figure 6:
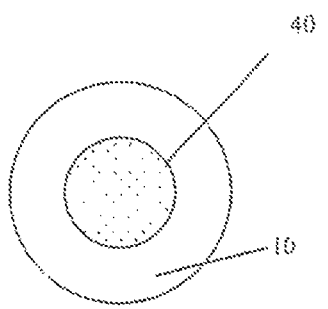
FIG. 6 is a schematic is a schematic of granulated lysine feed product comprising threonine 40 core and lysine freebase 10 shell.
Figure 7:
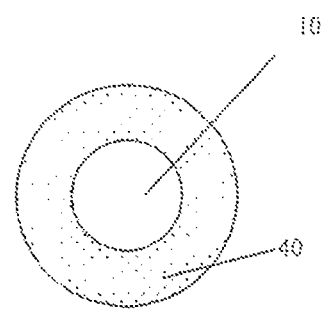
FIG. 7 is a schematic is of granulated lysine feed product comprising lysine freebase 10 core and threonine 40 shell.
Figure 8:
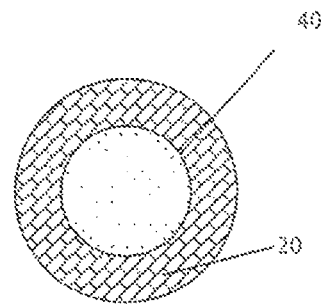
FIG. 8 is a schematic is of granulated lysine feed product comprising threonine 40 core and lysine hydrochloride 20 shell.
Figure 9:
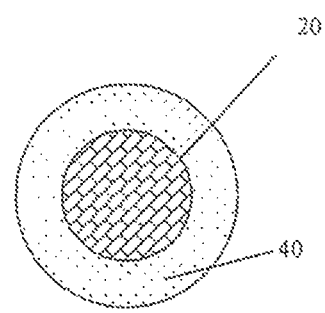
FIG. 9 is a schematic is of granulated lysine feed product comprising lysine hydrochloride 20 core and threonine 40 shell.

Another aspect may comprise an heteromorphic lysine containing granule that includes threonine. In one embodiment of this aspect, a core of threonine 40 is surrounded by a shell of lysine freebase 10 as depicted in FIG. 6. In another embodiment of this aspect, a core of lysine freebase 10 may be surrounded by a shell of threonine 40 as depicted in FIG. 7. Another non-limiting embodiment may comprise a core of threonine 40 surrounded by a shell of lysine hydrochloride 20 as depicted in FIG. 8. Yet another non-limiting embodiment may comprise a core of lysine hydrochloride 20 surrounded by a shell of threonine 40 as depicted in FIG. 9.

Figure 10:
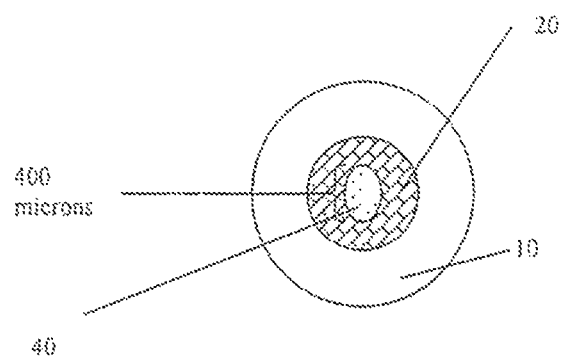
FIG. 10 is a schematic is of granulated lysine feed product comprising threonine 40 core surrounded by a lysine hydrochloride 20 shell which in turn is also surrounded by another shell of lysine freebase 10.
Figure 11:
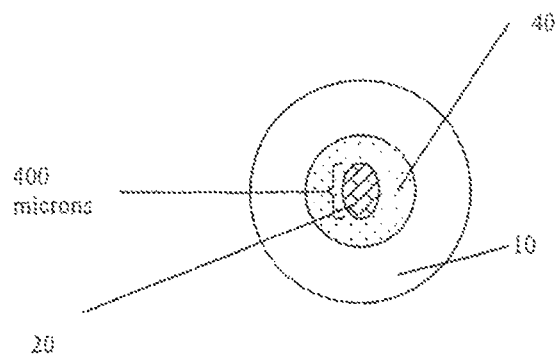
FIG. 11 is a schematic is of granulated lysine feed product comprising lysine hydrochloride 20 core surrounded by a threonine 40 shell which in turn is also surrounded by another shell of lysine 10 freebase.
Figure 12:
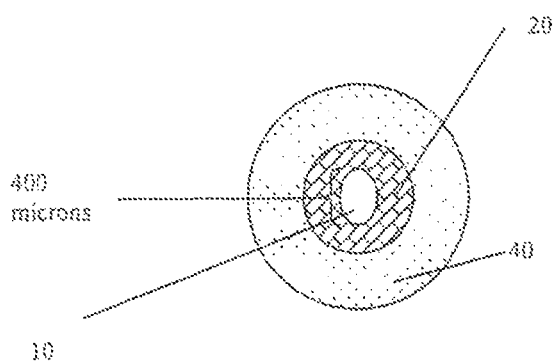
FIG. 12 is a schematic is of granulated lysine feed product comprising lysine freebase 10 core surrounded by a lysine hydrochloride 20 shell which in turn is also surrounded by another shell of threonine 40.

Yet another aspect may comprise a core of threonine 40 surrounded by a layer of lysine hydrochloride 20 surrounded by a shell of lysine freebase 10 as depicted in FIG. 10. In one particular embodiment, as depicted in FIG. 11, the core may be lysine hydrochloride 20 surrounded by a layer of threonine 40 surrounded by shell of lysine freebase 10. In another embodiment, as depicted in FIG. 12, the core may be lysine freebase 10, surrounded by a layer of lysine hydrochloride 20 surrounded by a shell of threonine 40.

In another aspect, lysine granules of a "raspberry morphology" or "cauliflower morphology" may be produced. In such case the granules thus obtained have a distorted or irregular morphology, which resembles that of "raspberries" or of "cauliflowers", rather than spherical beads. Such morphologies of the final product may also in another embodiment, have an irregular nonspherical morphology and a particle size distribution ranging from 10 μm to 800 μm.

Figure 13:
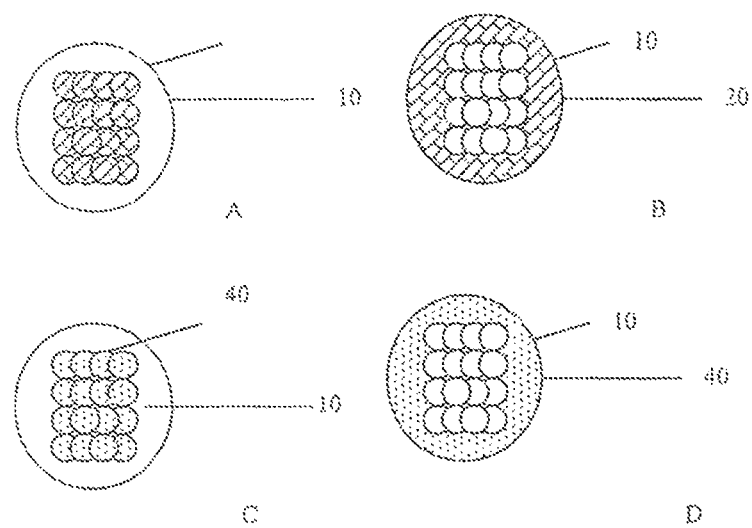
FIG. 13 is a schematic of granulated lysine feed products with different pluralities of cores of lysine freebase 10, lysine hydrochloride 20 or threonine 40 shells on cores of lysine freebase 10, lysine hydrochloride 20 or threonine 40 or a plurality thereof.

In one embodiment, the raspberry morphology as depicted in FIG. 13A includes several cores of irregular granules of lysine hydrochloride 20 surrounded by a shell of lysine freebase 10. In a particular embodiment as depicted in FIG. 13B, irregular granules of lysine freebase 10 may be surrounded by a shell of lysine hydrochloride 20.

In another embodiment, the raspberry morphology as depicted in FIG. 13C includes several cores of irregular granules of lysine freebase 10 surrounded by a shell of threonine 40, or in an alternative embodiment shown in FIG. 13D, cores of irregular granules threonine 40 surrounded by a shell of lysine freebase 10.

A still further aspect of the present teaching is a composition comprising lysine freebase, lysine hydrochloride or threonine granules primarily of gradient morphology, that is, wherein the composition of the particles gradually changes from the center to the surface of the granule.

A further aspect of the present teaching is a composition comprising lysine freebase, lysine hydrochloride or threonine granules primarily of interpenetrating network morphology wherein there are two co-continuous or co-centric shells of two different compositions creating an entangle.

A still further aspect of the present teaching is a composition comprising lysine freebase, lysine hydrochloride or threonine granules primarily of "salt-and-pepper" morphology wherein the particles are composed of two or more different compositions that are in separate domains.

Still another aspect of the present teaching is a composition comprising lysine freebase, lysine hydrochloride or threonine granules primarily of "ice-cream cone" morphology wherein two or more particles of different compositions, share a surface of contact that may be large or small.

Other morphologies that the particles may possess are "lobed" morphology, interpolymer morphology or "hairy particles" comprising lysine freebase, lysine hydrochloride or threonine granules.

Figure 14:
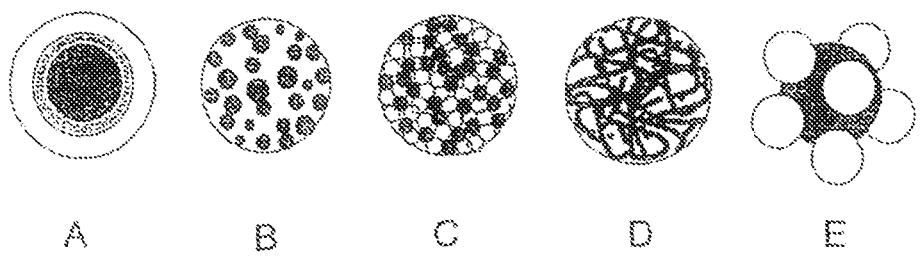
FIG. 14 is a schematic of representative particle morphologies.

A still further aspect of the present teaching is a composition comprising lysine freebase, lysine hydrochloride or threonine granules containing a combination of two or more morphologies mentioned above. Some of the morphologies discussed above are illustrated in FIG. 14.

The various embodiments of the onion or raspberry morphology described herein are understood to be non-limiting and one of ordinary skill in the art may tailor them suitably to obtain a desired flow behavior of the finished product.

Various non-limiting examples of lysine products suitable for use in the present disclosure include, but are not limited to, water soluble salts of lysine, such as, for example, lysine monohydrochloride ("lysine (HCl)"), lysine hydrate, lysine dihydrochloride, and lysine sulfate; lysine freebase; aqueous solutions of lysine freebase; granular lysine; lysine fermentation cell waste; lysine fermentation cell mass, lysine raffinate; a lysine mother liquor, or mixtures of any thereof.

According to other non-limiting embodiments, an aqueous solution of lysine freebase may be used, which may comprise an aqueous solution comprising from about 45% by weight to about 55% by weight of lysine freebase. In other non-limiting embodiments, the lysine content of the aqueous solution of lysine freebase may be increased as desired by either removal or lowering the amount of water in the solution or by the addition of an additional lysine product, such as a soluble salt of lysine, for example, lysine HCl and/or lysine sulfate. Alternatively, according to other non-limiting embodiments, the lysine content of the aqueous solution of lysine freebase may be decreased as desired by the addition of water to the solution.

Figure 15:
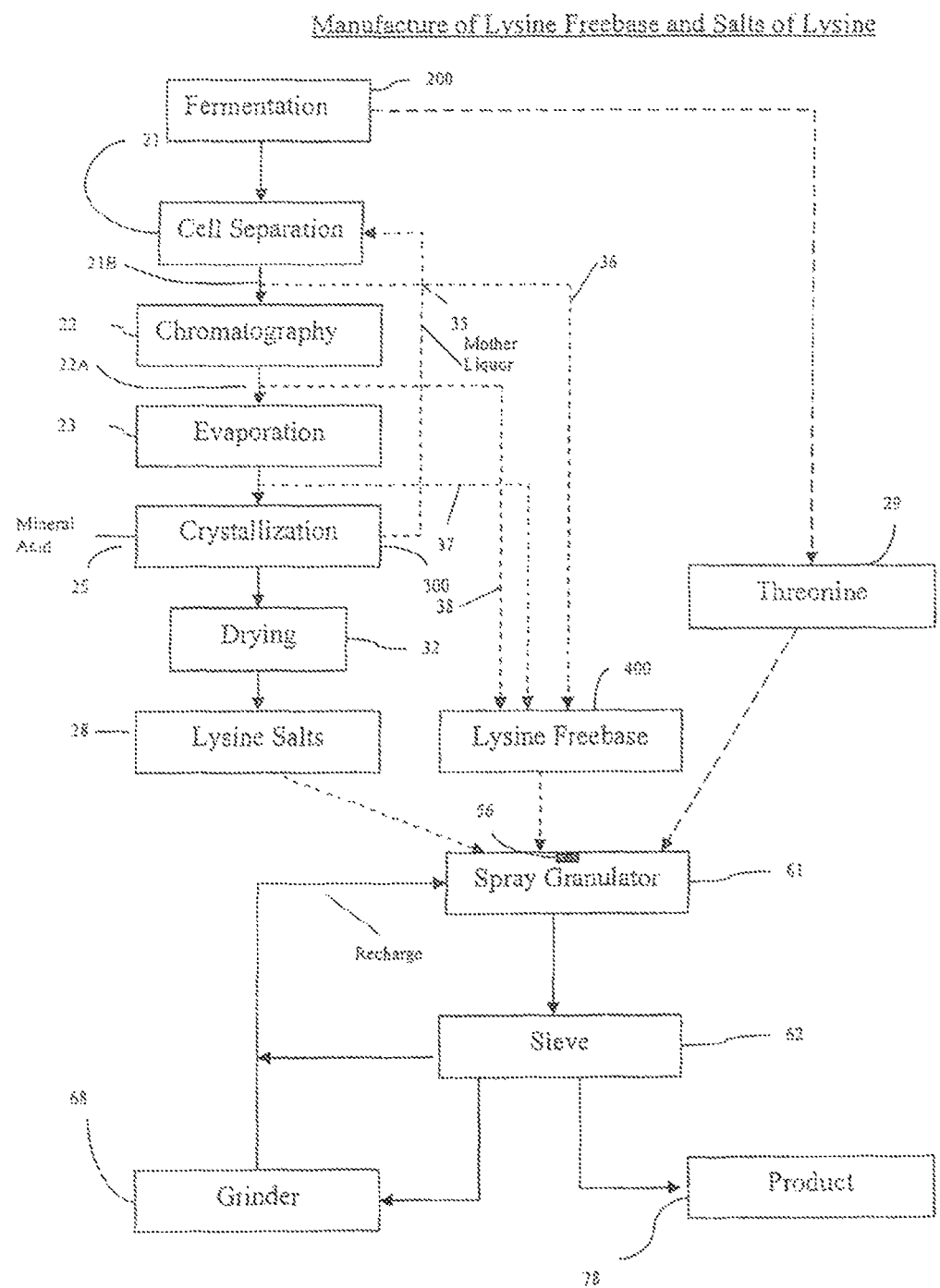
FIG. 15 is a flow chart, showing the principal steps in a process for making an amino acid feed supplement in which a salt of an amino acid is mixed with a freebase amino acid to produce a substantially dust free, free flowing granular amino acid product.

A method for preparing the heteromorphic granules described in the various embodiments of this disclosure is shown in the principle steps of an inventive process in FIG. 15. The processes described herein may be used to produce a lysine feed supplement with a final lysine purity in the range theoretically between about 35% and 80%. Fermentation 200 may be carried out by any suitable means described in the art such as for instance as describe in U.S. Pat. No. 6,017,555 the contents of in which, in their entirety are incorporated herein by reference.

After fermentation 200 a cell separation 21 may be used to separate the biomass and obtain a substantially cell-free lysine broth 21B. The cell free broth 21B is then processed through a chromatography step 22 to obtain a purified lysine freebase stream 22A. The lysine freebase is may then be subjected to evaporation 23 to increase its dry solids and acidified using a mineral acid 25 in a crystallizer 30 to crystallize salt of lysine, such as for example, lysine hydrochloride. The salt of lysine may then be dried in dryer 32.

The salt of lysine 28 may have a purity in a range between about 35% and 80% lysine, measured as a percent of freebase per kg. The lysine broth from the cell separation step may also be, in one embodiment, agglomerated with the salt of lysine by using a spray granulator 61 to provide particles of lysine in the core with particles of lysine or Threonine in the shell. The agglomerated particles, may also in one embodiment, be sifted in sieve 62 to provide the final lysine feed supplement 78. Oversized particles from sieve 62 may be processed through a grinder 68 and be used as "recharge" material for spray granulator 61.

In an alternate embodiment of the inventive process shown in FIG. 15, the lysine freebase 40 used in the spray granulator 61 may be obtained either from cell separation step 21, chromatography 22 or evaporation 23.

Figure 16:
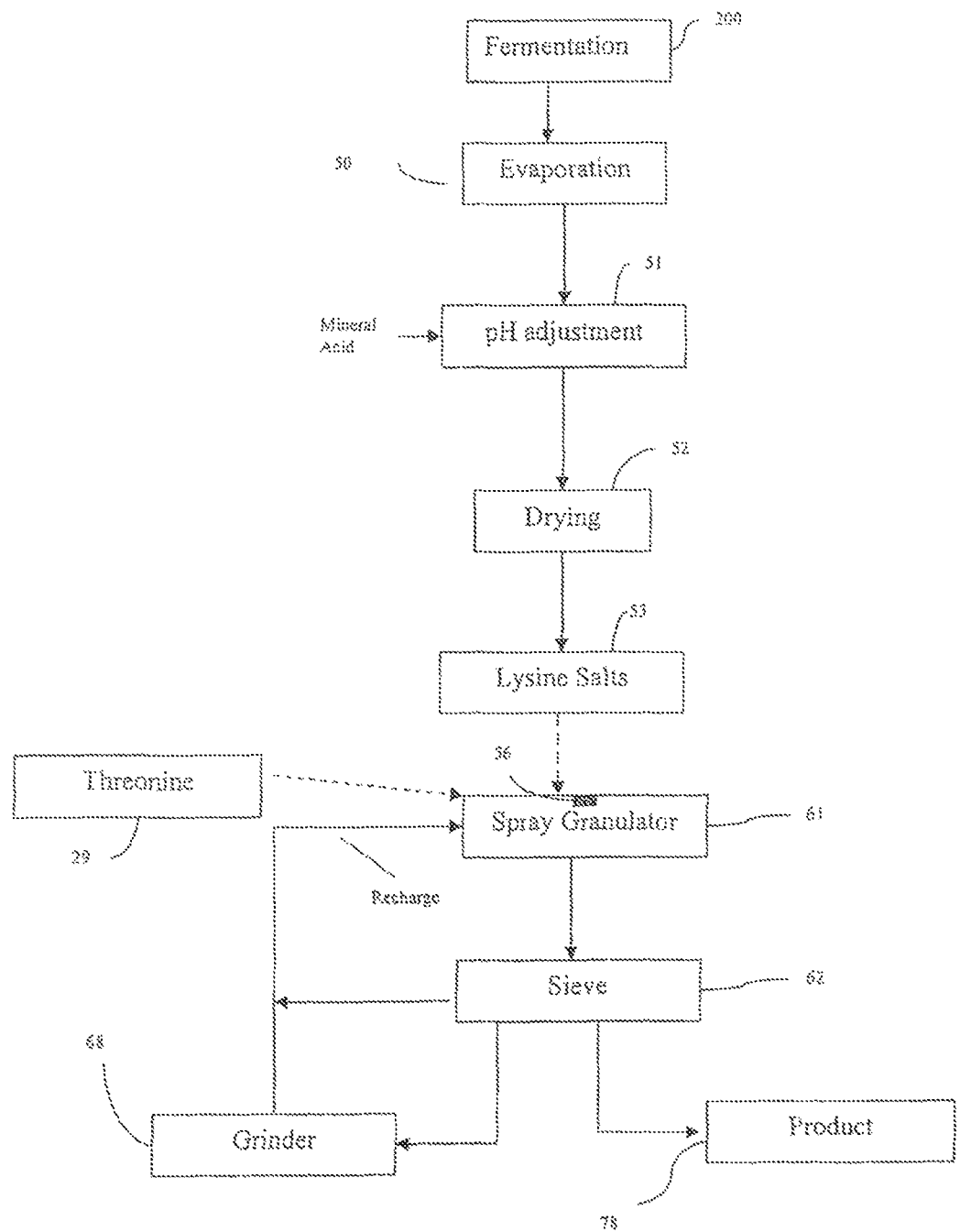
FIG. 16 is a flow chart, showing the principal steps in a process for making an amino acid feed supplement in which a salt of an amino acid is mixed with a freebase amino acid to produce a substantially dust free, free flowing granular amino acid product.

In another alternative embodiment of the inventive process shown in FIG. 16, the broth from fermentation 200 may be subjected to evaporation 50. After evaporation to increase its dry solids, the product may be acidified 51 using a mineral acid 60. The acidified product may then be dried 52 using techniques known in the art such as, but not limited to drum drying, spray drying, vacuum tray drying, vacuum belt drying etc. to obtain salts of lysine 53 which may serve as raw material for spray granulator 61.

In another embodiment threonine 29 (either freebase or a salt there of) may be added to the spray granulator 61 to obtain either a shell or a core containing the aforementioned amino acid.

In yet another embodiment threonine 29 may be replaced with any other suitable amino acid either in freebase form, or a salt there of, such as tryptophan, methionine etc.

In another embodiment sieve 62 and grinder 68 may be used to obtain an agglomerated product of the desired particle size.

In on aspect of this disclosure lysine freebase 400 may be obtained from any one of streams 36, 37 or 38. In one embodiment of this disclosure lysine freebase 400 may be mixed with small quantities of acid such that the stream 400 may be a mixture of lysine freebase and a salt of lysine.

In one aspect of this disclosure commercially available liquid lysine may be used as a base core in spray co-agglomeration with a lysine salt shell In one embodiment, the Liquid Lysine™ brand lysine is an approximately 50% (by weight) aqueous solution of lysine freebase obtained by concentrating lysine from a lysine fermentation broth.

In another aspect lysine monohydrochloride (HCl) may be used as a base core with a lysine freebase shell. lysine hydrochloride is commercially available in the form of lysine hydrochloride from Archer-Daniels-Midland Company, Decatur, Ill. Lysine hydrochloride may be obtained from, for example, but not limited to, purifying the product of a lysine fermentation process by crystallization of the hydrochloride salt. lysine hydrochloride (available from Archer-Daniels-Midland Company, Decatur, Ill., as well as other suppliers) may be utilized either as a granular solid or as an aqueous solution.

While another aspect of this disclosure is the harvesting and processing of lysine base from fermentation broth, the composition and nature of the fermentation medium may vary. For example, any suitable high lysine producing organism taken from the genus *E. Coli Corynebacterium* or *Brevibacterium* may be used to inoculate the fermentation medium. The pH is adjusted and maintained at approximately 7.2 with ammonium hydroxide. The temperature is maintained at about 32.degree C. The feed is Glucose and $(NH_4)_2SO_4$ with the glucose concentration initialized at about 10 g/l.

The fermentation medium can be inoculated into the fermentation vessel by using standard microbiological practices which are known to those skilled in the microbiology art. The fermentation vessel should be equipped with a stirrer, a ventilation system, and a temperature control device to maintain the fermentation at about 30 degree C. to about 32 degree C. The fermentation is carried out until the lysine base concentration is about 92 g/l (grams per liter) and the total dry solids is about 218 g/l. Aseptic techniques should be observed throughout the fermentation process to avoid a contamination of the fermentation broth with non-lysine producing organisms. The process produces a lysine feed supplement in the form of a substantially dust free, free flowing, granular lysine from fermentation broth comprising a salt of lysine co-granulated with lysine freebase.

In another embodiment, the substantially cell free enriched lysine broth is atomized by a nozzle 56 to provide an atomized spray of substantially cell free enriched lysine broth to make a percolating bed of lysine particulates in a spray granulator 61. The lysine particulates have a particle size of less than about 177 micron (i.e. particles that can pass through 80 mesh) and between the size range of about 100 micron and 177 micron. The bed of the spray granulator may be a fluidized bed of lysine particulates and is operated at a temperature between about 30 degrees C. and 100 degree C. The position of the nozzle 56 is adjusted until it is just above the fluidized bed of lysine particulates. Substantially cell free enriched lysine broth is sprayed onto the fluidized bed of lysine particulates to initiate the agglomeration process.

In an alternate embodiment a solution of lysine hydrochloride is sprayed onto the fluidized bed of lysine particulates to initiate the agglomeration process. In a yet another alternate embodiment a solution of threonine is sprayed onto the fluidized bed of lysine particulates to initiate the agglomeration process. In a further alternative embodiment a solution of tryptophan is sprayed onto the fluidized bed of lysine particulates to initiate the agglomeration process. The agglomeration process is allowed to continue to produce the substantially dust free, free flowing, granular lysine coated with a shell of lysine hydrochloride or threonine or lysine freebase, in the size range between approximately 177 micron and 1190 micron, or in the size range of between about 177 micron to 420 micron. The product is then screened and sorted for size at sieve 62. Granules at 62 that are too large (e.g. in the size range of greater than about 1190 micron) are ground in a grinder at 68 to a smaller particle size (e.g. in the size range of less than about 177 micron) and combined with material that is too small 84 (e.g. in the size range of less than about 177 micron) to produce recycled lysine particulates (shown "recharge" on FIGS. 14 and 15) and returned to the spray granulator 61 as a starting material which act as seeds for the agglomeration process. The substantially dust free, free flowing, granular lysine product in the size range of about 177 micron to 1190 micron pass through the sieving process and are acceptable as the end product at 78. However, a range is from about 177 micron to 420 micron may be used which can pack better and reduces cost for shipment.

The lysine concentration in the lysine fermentation broth may be about 90 g/l lysine to about 200 g/l lysine, measured as a percent of freebase per kg. However, the lysine concentration can vary from one fermentation run to the next. Hence, the use of a fermentation broth containing about 90 g/l lysine means that other suitable concentrations of lysine in the fermentation broth are acceptable. However, the lysine concentration in the fermentation broth should not be below about 30 g/l. Although ultrafiltration is the one method for obtaining the substantially cell free lysine broth in step 21 in FIG. 13, this does not mean other methods can not be used. The cells could also be removed by mechanical separation techniques, such as centrifugation. Other suitable methods include microfiltration and decanting.

This disclosure envisages the removal of cells from the lysine containing fermentation broth by various other processes. For example, the fermentation broth 20 could be split equally and about 50% centrifuged and the remaining 50% ultrafiltered with the outputs from both cell removal processes combined to produce a substantially cell free lysine broth. This flexibility will enhance the practice of the invention in an industrial setting. Although the present invention envisages the addition of material containing lysine to the substantially cell free concentrated lysine broth, the addition of such material to the concentrated lysine broth might be omitted altogether if the desired concentration of lysine (measured as freebase) is such that the addition is unnecessary. For example, the step of adding a material containing lysine might be omitted if the concentration of lysine in the substantially cell free concentrated lysine broth substantially exceeds about 35% lysine, measured as a percent of freebase per kg. If the cell free concentrated lysine broth contains substantially more than about 35% lysine, measured as a percent of freebase per kg, the lysine broth is a substantially cell free enriched lysine broth.

Experience has shown that there is a relationship between the orifice size of the nozzle 56, flow rate, and gauge pressure. While the nozzle size may be 0.0615", various other nozzles can also be used to supply the spray. In particular, nozzle designs supplied by Spraying Systems Co., PO Box 7900, Wheaton, Ill. 60189, USA work well to produce a fine spray. The spray granulator can be purchased from Glatt Air Techniques, 20 Spear Road, Ramsey, N.J. 07446-1288, USA.

Experience also suggests that manufacturing lysine granules on a commercial scale will require several nozzles to atomize and spray enriched lysine broth onto a proportionally larger bed of percolating particles of lysine.

The percolating bed of particles should comprise lysine particles of sufficiently small size to function as seeds for the agglomeration process. The lysine particulates may be less than about 177 micron in size and about 100 micron and 177 micron. In the agglomeration process, the seed particles simultaneously grow in size and are dried as they are sprayed with the enriched lysine permeate. The agglomeration process is aided by various components which are inherently present in the enriched lysine broth, namely: lysine fermentation broth, lysine hydrochloride, lysine sulfate and water. Such components may act as binder and are defined as substances which provide the sticky component to enable the seeds in the agglomeration process to build up in size.

The source of the lysine particulates used to produce and seed the fluidized bed of lysine in the spray granulator is not critical although the source is either obtained from atomizing the substantially cell free enriched lysine broth from step 53 in FIG. 15 or from recycled lysine particulates (described as "recharge" in FIG. 15).

Alternatively, the fluidized bed of lysine particulates could be produced by spray atomizing either a lysine containing fermentation broth, a substantially cell free lysine broth, and substantially cell free concentrated lysine broth or any mixture of these to produce a dry powder of lysine granules. Another example of a suitable source of the lysine particulates would be dry purified lysine hydrochloride powder and lysine sulfate which has been dried to a powder. The source of lysine particles may be sieved to remove lumps and sorted for particles less than about 177 micron (The may be in the size range between about 100 micron and 177 micron).

Experience has shown that the agglomeration process becomes self-sustaining by using the particles from recycling particles at 88 on either a batch or semi-continuous basis.

lysine has a C to N ratio of 3:1. The lysine products according to various non-limiting embodiments may comprise nitrogen content ranging from about 9% N to about 20% N, depending of the formulation. In certain embodiments, the nitrogen content of the lysine products may range from about 9% N to about 15% N.

In another aspect of this disclosure, the products produced using the embodiments described herein, may be used to produce fertilizer compositions, such as, those described in co-pending applications U.S. Provisional Application Ser. No. 60/726,749, filed Oct. 14, 2005, and U.S. Provisional Application Ser. No. 60/789,051, filed Apr. 3, 2006, the disclosures of which are incorporated in their entirety by reference herein.

In yet another additional non-limiting embodiment, mineral or mineral salts may be coated on the granules described herein to provide N-P-K nutritional value to the granules for use as for instance but not limited to animal feed, fertilizer, potting soil compositions, golf greens and lawn fertilizers, horticultural and agricultural fertilizers and mulches. Other suitable mineral or mineral salts include those containing zinc, manganese, magnesium, calcium or iron that may be combined alone or in combination with other minerals in the heteromorphic lysine granule.

In an additional non-limiting embodiment, the compositions described herein, may be produced at a first geographic location and transported or shipped to a second geographic location. For instance, a facility at the first geographic location may be able to produce a product more economically than a facility at the second location due to various factors. The factors may include, for example, lower costs of materials, lower costs of energy (e.g., electricity and/or natural gas or other petroleum products), lower costs of labor (e.g., wages paid to employees), lower costs of environmental controls or effects, or any other requirement for production of the compositions. Thus, the costs of producing the products in the first geographic location may be less than the costs of producing the products in the second geographic location, resulting in the production costs being less in the first geographic location.

In such an instance, the compositions may be produced at the first geographic location and shipped to the second geographic location such as by transport over water with ships or barges, trucking, flying, by rail, or other means of transportation. The geographic location may be a county, a state, a country, a continent, and/or combinations of any thereof. In this manner the product may be produced, for example, in a first county, state, country, or continent, and transported to and/or sold in a second county, state, country, or continent.

The examples below are only representative of some aspects of this disclosure. It will be understood by those skilled in the art that processes as set forth in the specification can be practiced with a variety of alterations with the benefit of the disclosure. These examples and the procedures used therein should not be interpreted as limiting this disclosure in any way not explicitly stated in the claims.

Example 1

In this embodiment manufacturing processes for heteromorphic lysine granules are described.

Three different process intermediate from the lysine manufacturing process described in FIGS. 15-16 are utilized as raw materials.

(a) Liquid lysine solutions with a nominal lysine concentration of 50% (Stream "A") but with an allowable range of 20%-80% solids.

(b) lysine hydrochloride solution that is used to feed the lysine hydrochloride crystallization step as described in FIG. 1 (Stream "B").

(c) Dry lysine hydrochloride final product (Stream "C")

The various feed streams (A, B, or C) may be used to produce an amino acid product as follows:

(1) Starting with a sample from the Stream "A", the product is dried to produce a liquid lysine powder with the desired moisture content.

(2) Starting with a sample from the Stream "A", the product is evaporated to raise the dry solids concentration and dried to obtain a free flowing lysine powder.

(3) Sample of Streams "A" and "B" is blended and dried to a desired moisture level.

(4) Sample of Streams "A" and "3" is blended and evaporated to a higher solids concentration. The evaporated product is dried to obtain a free flowing lysine powder.

(5) The product from tests 1 and 2 is spray coated with lysine hydrochloride using a spray agglomerator type dryer.

(6) The product from Stream "C" is spray coated with Stream "A" using a spray agglomerator type dryer.

(7) The products from tests 1-6, either by them selves or in combination is dry blended with Stream "C".

(8) The product of Stream "A" is pH adjusted to a target of 2.0-12.0 and dried to the desired moisture content.

(9) The product of Stream "A" is pH adjusted to a target of 2.0-12.0 and evaporated to raise the dry solids and dried to obtain a free flowing lysine powder.

Example 2

Run 2

In this Embodiment Coating on Lysine HCl of Lysine Freebase was Studied

A solution of 90 parts by volume of 725 g/l lysine freebase containing 70 percent dry solids was co-sprayed a solution of 10 parts by volume of lysine mother liquor (35 from FIG. 15) containing 50.8 percent dry solids and 320.4 g/l lysine freebase on a lysine HCL recharge using a spray granulator. An initial recharge of 250 g product was used. The inlet dryer temperature was kept at 275° F. and bed temperature was between 180° to 185° F. Feed was preheated to a temperature of 160° F. ad the dryer was sprayed at rates to keep the outlet temp greater than 159° F. Spray agglomeration was initially started at 8 ml/min for first 15 minutes and gradually increased to 20 ml/min as outlet temperatures permitted. A total of 1800 ml of lysine freebase and 900 ml of lysine HCL were used Spray agglomeration was continued until the weight of the bed reached 1.5 kg where in product was recovered, sieved and analyzed. Results are presented in Tables 1-3.

Example 3

Run 3

In this Embodiment Effect of Coating Lysine and Threonine Freebase on Lysine Salts was Studied A solution of 60 parts by volume of 725 g/l lysine freebase containing 70 percent dry solids was co-sprayed a solution of 40 parts by volume of threonine ultrafiltration concentrate blend containing 70 percent dry solids and 120 g/l threonine freebase on a lysine HCL recharge using a spray granulator. An initial recharge of 250 g product was used. The inlet dryer temperature was kept at 70 C and bed temperature was between 150-170 degrees F. Feed was preheated to a temperature of 100° F. ad the dryer was sprayed at rates to keep the outlet temp greater than 159° F. Spray agglomeration was initially started at 8 ml/min for first 15 minutes and gradually increased to 15 ml/min as outlet temperatures permitted Spray agglomeration was continued until the weight of the bed reached 1.5 kg wherein product was recovered, sieved and analyzed. Results are presented in Tables 1-3.

Example 4

Run 4

In this Embodiment Effect of Coating Lysine Freebase on Lysine Salts was Studied A solution of 80 parts by volume of 725 g/l lysine freebase containing 70 percent dry solids was co-sprayed a solution of 20 parts by volume of lysine freebase ultrafiltration concentrate blend containing 50 percent dry solids and 250 g/l lysine freebase on a lysine HCL recharge using a spray granulator. An initial recharge of 800 g product was used. The inlet dryer temperature was kept at 148 C and bed temperature was between 150-170 degrees F. Feed was preheated to a temperature of 71 C ad the dryer was sprayed at rates to keep the outlet temp greater than 148 C Spray agglomeration was initially started at 8 ml/min for first 15 minutes and gradually increased to 15 ml/min as outlet temperatures permitted. A total volume of 2000 ml feed was sprayed. Spray agglomeration was continued until the weight of the bed reached 1.3 kg where in product was recovered, sieved and analyzed. Results are presented in Tables 1-3.

Example 5

Run 5

In this Embodiment Effect of Coating Lysine Freebase and Lysine UF Concentrate on Lysine Salts was Studied A solution of 50 parts by volume of 725 g/l lysine freebase containing 70 percent dry solids was co-sprayed a solution of 50 parts by volume of lysine freebase ultrafiltration concentrate blend containing 50 percent dry solids and 250 g/l lysine freebase on a lysine HCL recharge using a spray granulator. An initial recharge of 800 g product was used. The inlet dryer temperature was kept at 148 C and bed temperature was between 150-170 degrees F. Feed was preheated to a temperature of 71 C ad the dryer was sprayed at rates to keep the outlet temp greater than 148 C. Spray agglomeration was initially started at 8 ml/min for first 15 minutes and gradually increased to 15 ml/min as outlet temperatures permitted. A total volume of 2000 ml feed was sprayed. Spray agglomeration was continued until the weight of the bed reached 1.3 kg where in product was recovered, sieved and analyzed. Results are presented in Tables 1-3.

Example 6

Run 6

In this Embodiment Effect of Coating Lysine Freebase and Lysine Mother Liquor on Lysine Salts was Studied A solution of 91 parts by volume of 725 g/l lysine freebase containing 70 percent dry solids was co-sprayed a solution of 9 parts by volume of lysine freebase mother liquor containing 48.3 percent dry solids and 320.4 g/l lysine freebase on a lysine HCL recharge using a spray granulator. An initial recharge of 400 g product was used. The inlet dryer temperature was kept at 148 C and bed temperature was between 150-170 degrees F. Feed was preheated to a temperature of 71 C ad the dryer was sprayed at rates to keep the outlet temp greater than 148 C. Spray agglomeration was initially started at 8 ml/min for first 15 minutes and gradually increased to 15 ml/min as outlet temperatures permitted. A total volume of 1850 ml feed was sprayed. Spray agglomeration was continued until the weight of the bed reached 1.915 kg where in product was recovered, sieved and analyzed. Results are presented in Tables 1-3.

Example 7

Run 7

In this Embodiment Effect of Coating Lysine Freebase and Lysine Mother Liquor on Lysine Salts was Studied A solution of 90 parts by volume of 725 g/l lysine freebase containing 70 percent dry solids was co-sprayed a solution of 10 parts by volume of lysine freebase mother liquor containing 44 percent dry solids and 320.4 g/l lysine freebase on a lysine HCL recharge using a spray granulator. An initial recharge of 400 g product was used. The inlet dryer temperature was kept at 70 C and bed temperature was between 140-160 degrees C. Feed was preheated to a temperature of 37.7 C ad the dryer was sprayed at rates to keep the outlet temp greater than 70 C. Spray agglomeration was initially started at 8 ml/min for first 15 minutes and gradually increased to 15 ml/min as outlet temperatures permitted. A total volume of 1800 ml feed was sprayed Spray agglomeration was continued until the weight of the bed reached 1.915 kg where in product was recovered, sieved and analyzed. Results are presented in Tables 1-3

Example 8

Run 6

In this Embodiment Effect of Coating Lysine Freebase and Lysine Mother Liquor on Lysine Salts was Studied A solution of 91 parts by volume of 725 g/l lysine freebase containing 70 percent dry solids was co-sprayed a solution of 1 part by volume of lysine freebase mother liquor containing 48.3 percent dry solids and 320.4 g/l lysine freebase on a lysine HCL recharge using a spray granulator. An initial recharge of 400 g product was used. The inlet dryer temperature was kept at 148 C and bed temperature was between 140-170 degrees C. Feed was preheated to a temperature of 71 C ad the dryer was sprayed at rates to keep the outlet temp greater than 148 C. Spray agglomeration was initially started at 8 ml/min for first 15 minutes and gradually increased to 15 ml/min as outlet temperatures permitted. A total volume of 1850 ml feed was sprayed. Spray agglomeration was continued until the weight of the bed reached 1.915 kg where in product was recovered, sieved and analyzed. Results are presented in Tables 1-3.

TABLE 1

| | | 2 | 3 | 4 | 5 | 6 | 7 | 8 |
|---|---|---|---|---|---|---|---|---|
| | | | | | Run Number | | | |
| | Feed Source | 70% Free base Lysine w/Lysine HCL final coat | 60/40 (V/V) L-Lysine Threonine UF concentrate blend | 80/20 (V/V) Lysinefree base and Lysine UF concentrate | 50/50 (V/V) Free base Lysine and lysine UF concentrate | 91/9 (V/V) Free base Lysine and lysine mother liquor | 90/10 (V/V) Free base Lysine and lysine mother liquor | 91/9 (V/V) Free base Lysine and lysine mother liquor |
| Feed A | | 1800 ml of 70% DS Lysine free base | 70% DS Lysine freebase containing 725 g/l Lysine | 70% DS Lysine freebase containing 725 g/l Lysine | 70% DS Lysine freebase containing 725 g/l Lysine | 70% DS Lysine freebase containing 725 g/l Lysine | 70% DS Lysine freebase containing 725 g/l Lysine | 70% TS Lysine freebase containing 725 g/l Lysine |

TABLE 1-continued

| | Run Number | | | | | | |
|---|---|---|---|---|---|---|---|
| | 2 | 3 | 4 | 5 | 6 | 7 | 8 |
| Feed Source | 70% Free base Lysine w/Lysine HCL final coat | 60/40 (V/V) L-Lysine Threonine UF concentrate blend | 80/20 (V/V) Lysinefree base and Lysine UF concentrate | 50/50 (V/V) Free base Lysine and lysine UF concentrate | 91/9 (V/V) Free base Lysine and lysine mother liquor | 90/10 (V/V) Free base Lysine and lysine mother liquor | 91/9 (V/V) Free base Lysine and lysine mother liquor |
| Feed B | No other feed mixture | 70% TS Threonine ~120-150 g/l | 50% UF ~240-260 g/l | 50% TS UF ~240-260 g/l | 48 3% DS Lysine free base | 44% DS Lysine free base containing 320 g/l Lysine | 48 3% DS Lysine free base |
| Final Coat | 900 mls of HCL lysine. | N/A | N/A | N/A | N/A | N/A | N/A |
| | Run conditions | | | | | | |
| Inlet temperature | 70 C. | 70 C. | 148 C. | 148 C. | 148 C. | 70 C. | Unavailable |
| Out temperature | 65-70 C. | 65-70 C. | 148 C. | 148 C. | 148 C. | 70 C. | Unavailable |
| Feed temperature | 37.7 C. | 37.7 C. | 71 C. | 71.1 C. | 71 C. | 37.7 C. | Unavailable |
| Feed rate | 20 ml/min. | 8-15 ml/min. | 8-15 ml/min. | 8-15 ml/min. | 8-15 ml/min. | 8-15 ml/min. | 8-15 ml/min. |
| Recharge Weight | .250 kg | | .800 kg | .800 kg | .400 kg. | Lysine HCL | .400 kg. |
| Recharge Source | Lysine HCL | Lysine HCL | Lysine HCL | Lysine HCL | Lysine HCL | 1800 ml total spray | Lysine HCL |
| Feed totals | 1800 mls L-lysine w/900 mls HCL coating | 1600 ml total spray | 2000 ml total spray | 2000 ml total spray | 1850 ml total spray | 1800 ml total spray | 1850 ml total spray |
| Final Weight | 1.500 kg | 1 400 kg | 1.3 kg | 1.300 kg | 1.915 kg | ~1 800 kg | 1.915 kg |

TABLE 2

Feed Analysis

| | Run Number | | | | | | |
|---|---|---|---|---|---|---|---|
| | 2 | 3 | 4 | 5 | 6 | 7 | 8 |
| pH of Feed | 9.2 | 9.8 | ~9.0-10.0 | ~9.0-10.0 | 9.8 | 9.8 | 9.8 |
| TS | 70.0% TS | 60 | ~60-70 | ~60-71 | ~60-72 | ~60-73 | ~60-74 |
| G/L Lysine | N/A | 491 | ~725 g/l +/− 50 g/l | ~725 g/l +/− 50 g/l | ~725 g/l +/− 50 g/l | ~725 g/l +/− 50 g/l | ~725 g/l +/− 50 g/l |

TABLE 3

Product Analysis

| | Run Number | | | | | | |
|---|---|---|---|---|---|---|---|
| | 2 | 3 | 4 | 5 | 6 | 7 | 8 |
| Bulk Density | 30.8 | 36 | 28.00% | 36.3 | 23.3 | 32.3 | 23.3 |
| +16 mesh | 0.00% | 3.00% | 4.00% | 1.40% | Unavailable | 1.00% | Unavailable |
| +40 mesh | 21.60% | 58.60% | 26.90% | 40.90% | Unavailable | 36.20% | Unavailable |
| +80 mesh | 72.20% | 38.10% | 69.80% | 52.50% | Unavailable | 65.30% | Unavailable |
| +Pan | 7.1% | 3.7 | 3 | 5.5 | Unavailable | 2 | Unavailable |
| Moisture | 0.50% | 1.20% | 2.10% | 1.30% | 2.20% | 1.50% | 2.20% |

TABLE 3-continued

Product Analysis

| | Run Number | | | | | | |
|---|---|---|---|---|---|---|---|
| | 2 | 3 | 4 | 5 | 6 | 7 | 8 |
| Purity by HPLC | 96.80% | 97.40% | 89.20% | 92.30% | 98.50% | 97.50% | 98.50% |
| Purity by Titration | 103.40% | 91.70% | 99.50% | 101.90% | 104.80% | 107.90% | 104.80% |

Example 9

In this embodiment caking tests on lysine granules prepared according to the various embodiments of this disclosure are performed.

A sample of 10.0 grams of product prepared according to various embodiments of this disclosure is stored in a glass vial and is exposed to various relative humidity conditions for 7 days before evacuation. Upon evacuation the products are examined visually a relative scale.

0=Flowed Easily, no clumps.
1=Needed a gentle tap to initiate flow.
2=Needed a sharp tap to initiate flow.
3=Solid cake.
4=Laden with water.

The caking tests are performed under the following conditions.

A. Relative humidity 33%, Temperature 30 degrees C.
B. Relative humidity 51%, Temperature 30 degrees C.
C. Relative humidity 63%, Temperature 30 degrees C.
D. Relative humidity 72.8%, Temperature 30 degrees C.
E. Relative humidity 84%, Temperature 30 degrees C.
F. Relative humidity 91%, Temperature 30 degrees C.

The granules prepared according to the various aspects of this disclosure are found to rate 0 or 1 on the relative scale indicating good flowability.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the disclosure and within the following claims.

We claim:

1. A heteromorphic lysine granule comprising an outer shell layer of at least one of dried lysine hydrochloride and an inner core region of dried lysine free base, wherein the particle is heteromorphic in form due to the interior core region consisting of a different material composition than the outer shell layer.

2. The heteromorphic lysine granule of claim 1 wherein the inner core region is comprised of the dried lysine salt admixed with the dried free lysine base wherein the lysine salt comprises between 10 percent and 80 percent of the granule.

3. The heteromorphic lysine granule of claim 1 wherein the inner core region consists of an innermost seed-of a-dried lysine hydrochloride, and a medial layer fraction coating the innermost fraction consisting of the dried lysine freebase.

4. The heteromorphic lysine granule of claim 1 wherein the dried lysine freebase is at 10-80% the weight of the granule, and wherein the granule absorbs less than 10% water when exposed to a temperature of 10 degrees Celsius to 50 degrees Celsius and a humidity of between 30% and 91% relative humidity for a period of 24 to 168 hours.

5. The heteromorphic lysine granule of claim 1 wherein the granule further includes at least one inorganic compound comprising at least one element selected from the group consisting of nitrogen, phosphorous, potassium, magnesium, manganese, iron and zinc.

6. A feed additive for ruminants that contains the heteromorphic lysine particle of claim 1.

7. The heteromorphic lysine granule of claim 1 wherein the granule has an irregular non-spherical morphology and a particle size distribution ranging from 10 μm to 800 μm and wherein a powder consisting of the heteromorphic granules is characterized as free flowing when exposed to a temperature of 10 degrees Celsius to 50 degrees Celsius and a humidity of between 30% and 91% relative humidity for a period of 24 to 168 hours.

8. The heteromorphic lysine granule of claim 1 having a multiphase morphology of roughly spherical shape wherein the inner core region comprises alternating layers of lysine freebase and lysine salt arranged concentrically, the alternating layers being finally surrounded by the outer coating of lysine hydrochloride.

9. A fertilizer composition that contains the heteromorphic lysine particle according to claim 1 wherein the heteropmorphic lysine particle further includes at least one mineral supplement selected from the group consisting of: an alkali metal salt, a nitrogen source, a phosphate source, and a potassium source.

10. The fertilizer composition according to claim 9 wherein the at least one mineral supplement is included in at least one of the outer shell layer or the inner core.

* * * * *